United States Patent
Chawla et al.

(10) Patent No.: US 9,456,981 B2
(45) Date of Patent: Oct. 4, 2016

(54) STABLE ORALLY DISINTEGRATING TABLETS OF HYOSCYAMINE

(71) Applicant: CADILA HEALTHCARE LIMITED, Ahmedabad, Gujarat (IN)

(72) Inventors: Manish Chawla, Gujarat (IN); Shailesh Biradar, Gujarat (IN); Ajay Kumar Sharma, Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 0 days.

(21) Appl. No.: 14/622,198

(22) Filed: Feb. 13, 2015

(65) Prior Publication Data

US 2015/0283068 A1 Oct. 8, 2015

(30) Foreign Application Priority Data

Feb. 13, 2014 (IN) .......................... 505/MUM/2014

(51) Int. Cl.
| | | |
|---|---|---|
| A61K 47/38 | (2006.01) | |
| A61K 9/00 | (2006.01) | |
| A61K 31/46 | (2006.01) | |
| A61K 47/18 | (2006.01) | |
| A61K 47/32 | (2006.01) | |
| A61K 9/20 | (2006.01) | |

(52) U.S. Cl.
CPC ........... *A61K 9/0056* (2013.01); *A61K 9/2054* (2013.01); *A61K 31/46* (2013.01); *A61K 47/183* (2013.01); *A61K 47/32* (2013.01); *A61K 47/38* (2013.01)

(58) Field of Classification Search
USPC ........................................ 424/477, 480, 484
See application file for complete search history.

(56) References Cited

U.S. PATENT DOCUMENTS

| | | |
|---|---|---|
| 5,464,632 A | 11/1995 | Cousin et al. |
| 6,149,938 A | 11/2000 | Bonadeo et al. |
| 7,282,217 B1 | 10/2007 | Grimshaw et al. |
| 7,425,341 B1 | 9/2008 | Grimshaw et al. |
| 8,840,924 B2 | 9/2014 | Tengler et al. |
| 2007/0202167 A1* | 8/2007 | Srinivasan ........... A61K 9/0095 424/468 |
| 2012/0219628 A1* | 8/2012 | Lim ..................... A61K 9/0056 424/484 |

* cited by examiner

*Primary Examiner* — Pancham Bakshi
(74) *Attorney, Agent, or Firm* — Ladas & Parry LLP

(57) ABSTRACT

The present invention relates to stable orally disintegrating tablets of hyoscyamine or pharmaceutically acceptable salts thereof. The invention also relates to processes for the preparation of such tablets and use thereof.

12 Claims, 1 Drawing Sheet

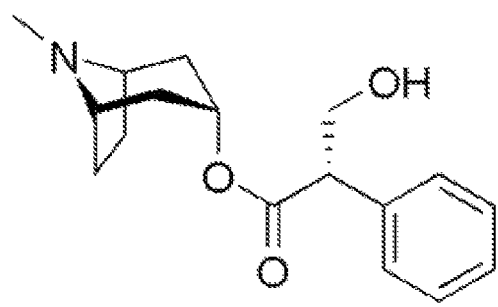

STABLE ORALLY DISINTEGRATING TABLETS OF HYOSCYAMINE

FIELD OF THE INVENTION

The present invention relates to stable orally disintegrating tablets of hyoscyamine or a pharmaceutically acceptable salt thereof. The invention also relates to processes for the preparation of such tablets and use thereof.

BACKGROUND OF THE INVENTION

The oral route of administration is considered as the most widely accepted route because of its convenience of self-administration, compactness and ease of manufacturing. Oral pharmaceutically accepted formulations, viz., liquid, pills, tablets, etc. generally include a multitude of ingredients, one or more of which are typically "active" ingredients. A pharmaceutical active ingredient is a substance having a specific physiological action and effect with minimal or no side effects. Thus, active ingredients are generally targeted for the treatment of specific symptoms, ailments, diseases, or disorders related to the body. Non-active ingredients, such as lubricants, colorants, flavoring agents, texture modifiers, disintegrants, preservatives, among others, generally referred to as "excipients", are commonly included with the active ingredient(s) to render the composition desirable in terms of its physical properties, aesthetic characteristics and stability.

Hyoscyamine (FIG. 1) also known as daturine is a tropane alkaloid. It is a secondary metabolite found in certain plants of the Solanaceae family, including henbane (*Hyoscyamus niger*), mandrake (*Mandragora officinarum*), jimsonweed (*Datura stramonium*), tomato (*Solanum lycopersicum*) and deadly nightshade (*Atropa belladonna*). It is the levorotary isomer of atropine (third of the three major nightshade alkaloids) and thus sometimes known as levo-atropine.

Hyoscyamine is an antagonist of muscarinic acetylcholine receptors (antimuscarinic). It blocks the action of acetylcholine at parasympathetic sites. It is used to provide symptomatic relief to various gastrointestinal disorders including spasms, peptic ulcers, irritable bowel syndrome, diverticulitis, pancreatitis, colic and cystitis. It has also been used to relieve some heart problems, control some of the symptoms of Parkinson's disease, as well as for control of respiratory secretions in palliative care. It may be useful in pain control for neuropathic pain treated with opioids as it increases the level of analgesia obtained. Several mechanisms are thought to contribute to this effect. The closely related drugs atropine and scopolamine and other members of the anticholinergic drug group like cyclobenzaprine, trihexyphenidyl, and orphenadrine are also used for this purpose. When hyoscyamine is used along with opioids or other anti-peristaltic agents, measures to prevent constipation are especially important given the risk of paralytic ileus.

U.S. Pat. No. 5,464,632 describes a tablet prepared by dry blending an active ingredient with a granulated carbohydrate, to form a composition, which is compressed to form the tablet.

U.S. Pat. No. 6,149,938 discloses a process for making a granulate composition suitable for the preparation of an oral solid form that can disintegrate rapidly inside the buccal cavity.

U.S. Pat. No. 7,282,217 discloses a rapidly disintegrating tablet comprising a compressed granulate containing hyoscyamine, directly compressible spray-dried mannitol; and directly compressible microcrystalline cellulose. It also discloses a rapidly disintegrating tablet comprising an active ingredient, a water soluble, directly compressible carbohydrate, and a water soluble, directly compressible filler.

U.S. Pat. No. 7,425,341 discloses a method of producing a rapidly disintegrating tablet of hyoscyamine. The method comprises wet granulating a mixture comprising a directly compressible water soluble carbohydrate; a, water insoluble filler, hyoscyamine sulfate, and a solvent, and compressing the granulate to produce the tablet.

U.S. Pat. No. 8,840,924 discloses a rapidly dissolving, taste-masked hyoscyamine pharmaceutical composition comprising a hyoscyamine-resin complex, one or more amorphous sugars and a compressible, free-flowing, pharmaceutical, taste-masking excipient.

There are number of medications or pharmaceutical compositions available for hyoscyamine sulfate. NuLev®, chewable melt tablets of hyoscyamine sulfate, marketed by Alaven Pharmaceuticals in USA contained inactive ingredients lactose monohydrate, magnesium stearate, mannitol USP, peppermint flavor, starch and stearic acid. Anaspaz®, the orally disintegrating tablets of hyoscyamine sulfate, marketed by B.F. Ascher and Co., Inc. in USA contained inactive ingredients lactose, magnesium stearate, mannitol, sorbitol, pregelatinized starch and stearic acid.

The stability of hyoscyamine sulfate in oral dosage form is still a matter of concern due to the presence of impurities in the formulation. As reported in the literature that hyoscyamine sulfate contains seven impurities, viz., DL-tropic acid, 7-hydroxyhyoscyamine, 6-hydroxyhyoscyamine, scopolamine, norhyoscyamine, apoatropine and littorine. The mechanism of formation of each impurity is different and based on some scientific principles. Impurities are formed because of gradual degradation of active ingredient in the composition. Usually, the degradation is chemical, i.e., active ingredient is altered at a chemical level thereby affecting its activity as well as the overall stability and usefulness of the composition. The stability issues generally adversely affect the costs of commercializing the composition. Hence, there is a need to develop a storage-stable dosage form of hyoscyamine sulfate with increased shelf-life and method of preparing thereof.

SUMMARY OF THE INVENTION

In one general aspect, there is provided a stable orally disintegrating tablet comprising hyoscyamine or a pharmaceutically acceptable salt thereof and one or more amino acids.

Embodiments of the present invention may include one or more of the following features. For example, the orally disintegrating tablet may further include one or more pharmaceutical acceptable excipients. The pharmaceutical acceptable excipients may include one or more diluents, fillers/bulking agents, disintegrants, binders, stabilizing agents, antioxidants, glidants, lubricants, sweeteners/taste masking agents, colorants, flavors, and the like.

The stable orally disintegrating tablet may retain at least about 80% of the potency of hyoscyamine after storing the tablet for three months at 40° C. and 75% relative humidity.

The stable orally disintegrating tablet may have a weight of less than about 70 mg. In another aspect, there is provided a stable orally disintegrating tablet comprising hyoscyamine sulfate, wherein the tablet comprises about 0.1-1.0% w/w of hyoscyamine sulfate and about 10-50% w/w of an amino acid.

In another aspect, there is provided a stable orally disintegrating tablet comprising hyoscyamine sulfate and one or more amino acids selected from the group consisting of aspargine, alanine, glutamic acid, glycine, proline and threonine.

In another aspect, there is provided a stable orally disintegrating tablet comprising hyoscyamine sulfate, glycine and one or more pharmaceutically acceptable excipients.

In another aspect, there is provided a stable orally disintegrating tablet comprising hyoscyamine sulfate, glycine, aspartame, crospovidone and microcrystalline cellulose.

In another aspect, there is provided a stable orally disintegrating tablet comprising: 0.1-1.0% w/w of hyoscyamine sulfate, 50-65% w/w of microcrystalline cellulose, 25-35% w/w of glycine, 1.0-3.0% w/w of aspartame; and 2.0-10% w/w of crospovidone.

In another aspect, there is provided a process for preparing a stable orally disintegrating tablet of hyoscyamine or a pharmaceutically acceptable salt thereof. The process includes:
i. preparing aqueous solution or suspension of hyoscyamine or a pharmaceutically acceptable salt thereof;
ii. granulating an excipient with the solution or suspension of hyoscyamine;
iii. drying the granules and mixing the granules with an amino acid and one or more pharmaceutically acceptable excipients;
iv. lubricating the mixture obtained; and
v. compressing the lubricated mixture to obtain the tablets.

In another aspect, there is provided a process for preparing a stable orally disintegrating tablet of hyoscyamine or a pharmaceutically acceptable salt thereof. The process includes:
i. mixing hyoscyamine or a pharmaceutically acceptable salt thereof with one or more pharmaceutically acceptable excipients;
ii. granulating the mixture;
iii. drying the granules and mixing the granules with an amino acid and one or more pharmaceutically acceptable excipients;
iv. lubricating the mixture obtained; and
v. compressing the lubricated mixture to obtain the tablets.

In another aspect, there is provided a process for preparing a stable orally disintegrating tablet of hyoscyamine or a pharmaceutically acceptable salt thereof. The process includes:
i. mixing hyoscyamine or a pharmaceutically acceptable salt thereof with an amino acid and one or more pharmaceutically acceptable excipients;
ii. granulating the mixture;
iii. drying the granules and mixing the granules with one or more pharmaceutically acceptable excipients;
iv. lubricating the mixture obtained; and
v. compressing the lubricated mixture to obtain the tablets.

Embodiments of the process may include one or more of the following features. For example, the tablet may include one or more pharmaceutical acceptable excipients selected from diluents, fillers/bulking agents, disintegrants, binders, stabilizing agents, antioxidants, glidants, lubricants, sweeteners/taste masking agents, colorants, flavors, and the like. The tablet may retain at least about 80% of the potency of hyoscyamine after storing the tablet for three months at 40° C. and 75% relative humidity.

In yet another general aspect, there is provided a method of treatment of peptic ulcer and irritable bowel syndrome (irritable colon, spastic colon, mucous colitis), acute enterocolitis, disease associated with gastric secretion, visceral spasm, hypermotility in cystitis, pylorospasm and associated abdominal cramps, biliary and renal colic psychosis in a patient comprising administering to said subject an orally disintegrating tablets of hyoscyamine or a pharmaceutically acceptable salt comprising an amino acid.

The details of one or more embodiments of the present invention are set forth in the description below. Other features, objects and advantages of the invention will be apparent from the description.

DESCRIPTION OF THE DRAWING

FIG. 1 is hyoscyamine, also known as daturine, which is a tropane alkaloid.

DETAILED DESCRIPTION OF THE INVENTION

The inventors of the invention have surprisingly found that it is possible to develop stable orally disintegrating tablets of hyoscyamine sulfate using one or more amino acids. Such tablets can also remain stable and retain at least 80% of the potency of hyoscyamine sulfate after storage for three months at 40° C. and 75% relative humidity. Without being bound by any particular theory, it is believed that less degradants or impurities may be generated during processing of hyoscyamine or a pharmaceutically acceptable salt thereof, manufacturing of the composition or by degradation of hyoscyamine or a pharmaceutically acceptable salt thereof upon storage of the composition. We have surprisingly found that the orally disintegrating tablets prepared by using an amino acid generate lesser impurities upon storage as compared to the orally disintegrating tablets prepared without using such amino acids.

Orally disintegrating tablets of hyoscyamine can disintegrate/dissolve in the mouth rapidly without administering extra water. Such dosage forms may provide the convenience of a tablet formulation while allowing the rapid bioavailability of drug. Such dosage forms due to their ease of administration and pleasant mouth feel, may encourage patients especially children, the elderly patients who have difficulty in swallowing conventional tablets to adhere to daily medication regimens and also allow the luxury of much more accurate dosing than oral liquids. Yet another situation where such compositions would be useful, where water may not be readily available to assist in swallowing the tablet in specific conditions.

The term "orally disintegrating tablet" or "orally disintegrating pharmaceutical composition" is defined as "A solid dosage form containing medicinal substance or active ingredient which disintegrates rapidly usually within a matter of seconds when placed in oral cavity." The disintegration time for orally disintegrating tablets generally range from several seconds to about a minute. The tablets of the present invention disintegrate in time ranged from a few seconds to longer than a minute, and preferably disintegrate in time approximately 30 seconds or less.

The term "hyoscyamine" is used in a broad sense to include not only the hyoscyamine per se but also its pharmaceutically acceptable salts, pharmaceutically acceptable solvates, pharmaceutically acceptable hydrates, pharmaceutically acceptable enantiomers, pharmaceutically acceptable derivatives, pharmaceutically acceptable polymorphs and pharmaceutically acceptable prodrugs thereof. Preferred salt of hyoscyamine used in the current invention is hyoscyamine sulfate. The amount of hyoscyamine sulfate used in the tablet may be from about 0.1 to about 10% by weight of the tablet.

The term "stable" herein refers to at least 80% of the potency of the drug substance is retained during the three months storage at 40° C./75% RH without significant change in the rate and extent to which the drug substance is released from the product. In certain particularly preferred embodiments, longer stability may be observed, for example at least 90% of potency of hyoscyamine may be retained during six months storage at 40° C./75% RH and/or nine months or twelve months storage at 25° C./60% RH without significant change in the rate and extent to which hyoscyamine is released from the tablets. The term "significant change" herein refers to more than about 10-15% change. As per ICH guideline, the known impurities or degradants must not be more than 1% and unknown impurities must not be more than 0.5% each in the composition, when stored in appropriate pack at 40° C./75% RH for six months.

Amino acids are biologically important organic compounds composed of amine (—$NH_2$) and carboxylic acid (—COOH) functional groups, along with a side-chain specific to each amino acid. The key elements of an amino acid are carbon, hydrogen, oxygen, and nitrogen, though other elements are found in the side-chains of certain amino acids. About 500 amino acids are known and can be classified in many ways. They can be classified according to the core structural functional groups locations as alpha- ($\alpha$-), beta- ($\beta$-), gamma- ($\gamma$-) or delta- ($\delta$-) amino acids; other categories relate to polarity, pH level, and side-chain group type (aliphatic, acyclic, aromatic, containing hydroxyl or sulfur, etc.). The amino acid may be selected from Aliphatic amino acid (Glycine, Alanine, Valine, Leucine, Isoleucine), Hydroxyl or Sulfur/Selenium-containing amino acid (Serine, Cysteine, Selenocysteine, Threonine, Methionine, Cyclic (Proline), Aromatic amino acid (Phenylalanine, Tyrosine, Tryptophan), Basic amino acid (Histidine, Lysine, Arginine), Acidic and their Amide containing amino acid (Aspartate, Glutamate, Asparagine, Glutamine). Preferred amino acids may include one or more of aspargine, alanine, glutamic acid, glycine, proline, threonine, and the like. The most preferred amino acid used is glycine. The amount of amino acid used in the tablet may be from about 10 to about 50%, preferably from about 25 to about 35% by weight of the tablet.

In one embodiment, a stable orally disintegrating tablet comprises hyoscyamine or a pharmaceutically acceptable salt thereof, an amino acid and one or more pharmaceutically acceptable excipients.

In another embodiment, a stable orally disintegrating tablet may comprise nonpareil sugar spheres/beads or inner seeds coated with hyoscyamine or a pharmaceutically acceptable salt thereof, which may be further coated with one or more polymer/s, surfactant's, antioxidant's or pharmaceutically acceptable excipients. Preferably, the inner core is made of inert nonpareil sugar spheres, microcrystalline cellulose, mannitol, lactose, and the like.

In another embodiment, a stable orally disintegrating tablet comprises hyoscyamine sulfate, glycine, aspartame, crospovidone and microcrystalline cellulose.

As per the invention, a stable orally disintegrating tablet of hyoscyamine sulfate may be prepared, wherein the tablet has a weight of less than 70 mg preferably less than 60 mg, most preferably less than or equal to 50 mg.

In other embodiments, a stable orally disintegrating tablet comprising hyoscyamine sulfate may be prepared, wherein the tablet retains at least 80% potency of hyoscyamine sulfate after storing the tablet at 40° C. and 75% relative humidity for three months.

In a preferred embodiment, a stable orally disintegrating tablet comprises 0.1-1.0% w/w of hyoscyamine sulfate, 50-65% w/w of microcrystalline cellulose, 25-35% w/w of glycine, 1.0-3.0% w/w of aspartame; and 2.0-10% w/w of crospovidone.

The pharmaceutically acceptable excipients may be present as extragranular or intragranular excipients and may include one or more of diluents, fillers/bulking agents, disintegrants, binders, stabilizing agents, antioxidants, glidants, lubricants, sweeteners/taste masking agents, colorants and flavors.

Suitable diluents/fillers or bulking agents include, but are not limited to, saccharides, including monosaccharides, disaccharides, polysaccharides and sugar alcohols such as arabinose, lactose, dextrose, sucrose, fructose, maltose, mannitol, erythritol, sorbitol, xylitol lactitol, and other bulking agents such as powdered cellulose, microcrystalline cellulose, sugar and derivatives thereof.

Suitable binders include, but are not limited to, one or more of methyl cellulose, hydroxypropyl cellulose (HPC), hydroxypropyl methyl cellulose (HPMC), sugars, starch, polyvinyl pyrrolidone (PVP), gelatin, gum Arabic, ethyl cellulose, polyvinyl alcohol, tragacanth, sodium alginate, acrylate, methacrylate or phthalate polymers or copolymers thereof.

Suitable disintegrants include, but are not limited to, croscarmellose sodium, crospovidone, sodium starch glycolate, corn starch, potato starch, maize starch and modified starches, calcium silicates, low substituted hydroxy-propylcellulose. Suitable super-disintegrants includes, but are not limited to, cross-linked cellulose, a cross-linked polymer and a cross-linked starch such as croscarmellose sodium, crospovidone and sodium starch glycolate or commercially available grades such as Ludipress®, Cellactose® and Starlac®.

Suitable stabilizers that may be used comprise alkali-metals and alkaline earth metals, bases of phosphates and organic acid salts and organic amines, natural gums such as xanthan gum, locust bean gum, carrageenan, guar gum or mixtures thereof.

Suitable antioxidants include, but are not limited to, butylated hydroxanisole, sodium ascorbate, butylated hydroxytoluene, sodium metabisulfate, alpha tocopherol, malic acid, citric acid, ascorbic acid; and the like.

Suitable lubricants and glidants include, but are not limited to, stearic acid and its derivatives or esters like sodium stearate, magnesium stearate and calcium stearate and the corresponding esters such as sodium stearyl fumarate; talc and colloidal silicon dioxide respectively.

Suitable taste masking agents include, but are not limited to, one or more of polymers, surfactants, sweeteners and flavors. Examples of polymers include one or more of cellulose acetate, polymethacrylates, hydroxypropylmethyl cellulose, hydroxypropyl cellulose, hydroxylethyl cellulose; and the like. Examples of sweeteners include but not limiting to one or more of aspartame, saccharin, sucralose, glycyrrhizin; and the like.

Suitable sweeteners include, but are not limited to, saccharides such as aspartame, sucrose, dextrose, glucose, maltose, dextrins, D-tagatose, trehalose, dried invert sugar, fructose, levulose, galactose, corn syrup solids, and the like, alone or in combination. Other examples of sweeteners comprise sodium saccharin; aspartame; sugarless sweeteners including polyhydric alcohols such as sorbitol, mannitol, xylitol, glycerol, hydrogenated starch hydrolysates, maltitol, isomaltitol, erythritol, lactitol and the like, alone or in combination.

Suitable flavors include, but are not limited to, citric acid, cinnamon, wintergreen, eucalyptus, spearmint, peppermint, menthol, anise as well as fruit flavors such as apple, pear, peach, vanilla, strawberry, cherry, apricot, orange, watermelon, banana and the like; bean-derived flavors, such as coffee, cocoa and the like or mixtures thereof.

The stable orally disintegrating tablets of hyoscyamine or a pharmaceutically acceptable salt thereof can be prepared by any suitable method known in the art, such as direct compression, dry granulation, wet granulation, fluidized bed granulation, melt extrusion, melt granulation, spray granulation, spray coating, freeze drying, spray drying and solvent evaporation.

Alternatively, hyoscyamine or a pharmaceutically acceptable salt thereof may be mixed, coated, sprayed, granulated or complexed with one or more pharmaceutically acceptable excipients to formulate the stable orally disintegrating tablet.

In an embodiment, the process of preparing stable orally disintegrating tablets of hyoscyamine or a pharmaceutically acceptable salt thereof comprises a step of compressing the admixture of hyoscyamine or a pharmaceutically acceptable salt thereof with one or more pharmaceutical excipients into tablets.

In a further embodiment, a stable orally disintegrating tablet of hyoscyamine or a pharmaceutically acceptable salt thereof made by a process comprising a step of wet granulating hyoscyamine or a pharmaceutically acceptable salt thereof with one or more pharmaceutical excipients, optionally processing the resultant granules into suitable dosage form such as tablets.

In yet another embodiment, a stable orally disintegrating tablet of hyoscyamine or a pharmaceutically acceptable salt thereof made by a process comprising a step of spray granulating hyoscyamine or a pharmaceutically acceptable salt thereof with one or more pharmaceutical excipients, optionally processing the resultant granules into suitable dosage form such as tablets.

In yet another embodiment, a stable orally disintegrating tablet of hyoscyamine or a pharmaceutically acceptable salt thereof made by a process comprising
 i. preparing aqueous solution or suspension of hyoscyamine or a pharmaceutically acceptable salt thereof;
 ii. granulating an excipient with the solution or suspension of hyoscyamine;
 iii. drying the granules and mixing the granules with an amino acid and one or more pharmaceutically acceptable excipients;
 iv. lubricating the mixture obtained; and
 v. compressing the lubricated mixture to obtain the tablets.

In yet another embodiment, a stable orally disintegrating tablet of hyoscyamine or a pharmaceutically acceptable salt thereof made by a process comprising
 i. mixing hyoscyamine or a pharmaceutically acceptable salt thereof with one or more pharmaceutically acceptable excipients;
 ii. granulating the mixture;
 iii. drying the granules and mixing the granules with an amino acid and one or more pharmaceutically acceptable excipients;
 iv. lubricating the mixture obtained; and
 v. compressing the lubricated mixture to obtain the tablets.

In yet another embodiment, a stable orally disintegrating tablet of hyoscyamine or a pharmaceutically acceptable salt thereof made by a process comprising
 i. mixing hyoscyamine or a pharmaceutically acceptable salt thereof with an amino acid and one or more pharmaceutically acceptable excipients;
 ii. granulating the mixture;
 iii. drying the granules and mixing the granules with one or more pharmaceutically acceptable excipients;
 iv. lubricating the mixture obtained; and
 v. compressing the lubricated mixture to obtain the tablets.

In yet another embodiment, a method of treatment of peptic ulcer and irritable bowel syndrome (irritable colon, spastic colon, mucous colitis), acute entercolitis, disease associated with gastric secretion, visceral spasm, hypermotility in cystitis, pylorospasm and associated abdominal cramps, biliary and renal colic psychosis in a patient comprises administering to said subject an orally disintegrating tablets of hyoscyamine or a pharmaceutically acceptable salt comprising an amino acid.

The invention is further illustrated by the following examples which are provided to be exemplary of the invention and do not limit the scope of the invention. While the present invention has been described in terms of its specific embodiments, certain modifications and equivalents will be apparent to those skilled in the art and are intended to be included within the scope of the present invention.

Example 1

TABLE 1A

| Sr. No. | Name of Ingredient | Quantity (mg/tablet) | Quantity (% w/w) |
|---|---|---|---|
| 1 | Hyoscyamine sulfate | 0.125 | 0.25 |
| 2 | Microcrystalline cellulose | 29.025 | 58.05 |
| 3 | Glycine | 15.00 | 30.00 |
| 4 | Aspartame | 1.00 | 2.00 |
| 5 | Crospovidone | 3.00 | 6.00 |
| 6 | Mint flavor | 0.35 | 0.70 |
| 7 | Colloidal silicon dioxide | 1.00 | 2.00 |
| 8 | Magnesium stearate | 0.50 | 1.00 |
| 9 | Purified water | q.s. | q.s. |
| | Total | 50.00 | 100.00 |

Procedure:

Hyoscyamine sulfate was dissolved in purified water. Microcrystalline cellulose was granulated with the use of solution of hyoscyamine sulfate. The granules were dried and mixed with glycine, aspartame, crospovidone, mint flavor and colloidal silicon dioxide. The mixture was lubricated with magnesium stearate. The lubricated blend was compressed into tablets.

The tablets of Example 1 were charged on stability in HDPE pack at 40° C. and 75% relative humidity for 6 months. The results of stability study summarized in Table 1B show that the tablets remain stable for at least 6 months when stored in the conditions described above.

TABLE 1B

| Impurity | Initial | 1 Month | 3 Months | 6 Months |
|---|---|---|---|---|
| DL-tropic acid | ND* | ND | ND | ND |
| 7-hydroxy hyoscyamine | ND | ND | ND | ND |
| 6-hydroxy hyoscyamine | ND | ND | ND | ND |
| Scopolamine | ND | ND | ND | ND |

TABLE 1B-continued

| Impurity | Initial | 1 Month | 3 Months | 6 Months |
|---|---|---|---|---|
| Norhyoscyamine | ND | ND | ND | ND |
| Apoatropine | ND | 0.03 | 0.05 | 0.07 |
| Littorine | ND | ND | ND | ND |
| Maximum unknown | 0.04 | 0.05 | 0.15 | 0.11 |
| Total impurities | 0.04 | 0.08 | 0.23 | 0.33 |

*ND = Not Detected

Example 2

TABLE 2

| Sr. No. | Name of Ingredient | Quantity (mg/tablet) | | | |
|---|---|---|---|---|---|
| | | Example 2a | Example 2b | Example 2c | Example 2d |
| 1 | Hyoscyamine sulfate | 0.125 | 0.125 | 0.125 | 0.125 |
| 2 | Microcrystalline cellulose | 22.875 | 32.875 | 37.875 | 17.875 |
| 3 | Glycine | 20.000 | 10.000 | 5.000 | 25.000 |
| 4 | Purified water | q.s. | q.s. | q.s. | q.s. |
| 5 | Crospovidone | 3.000 | 3.000 | 3.000 | 3.000 |
| 8 | Mint flavor | 1.000 | 1.000 | 1.000 | 1.000 |
| 7 | Aspartame | 1.000 | 1.000 | 1.000 | 1.000 |
| 8 | Silicon dioxide | 1.000 | 1.000 | 1.000 | 1.000 |
| 9 | Magnesium stearate | 1.000 | 1.000 | 1.000 | 1.000 |
| | Total | 50.000 | 50.000 | 50.000 | 50.000 |

Procedure:

Hyoscyamine sulfate, microcrystalline cellulose and glycine were sifted through a 20 mesh sieve and the sifted blend was loaded into a rapid mixer granulator to form granules. The mixture was blended with purified water. The wet mass was dried in a fluid bed dryer. The dried granules were sifted through a 30 mesh sieve size and the oversized granules were milled. Crospovidone, mint flavor and aspartame were sifted through a 40 mesh sieve and the sifted material was mixed with granules and loaded in the blender. Silicon dioxide and magnesium stearate was sifted through a 40 mesh sieve and lubricated the above material. The lubricated granules were compressed into tablets.

Comparative Example 1

TABLE 3

| Sr. No. | Name of Ingredient | Quantity (% w/w) |
|---|---|---|
| 1 | Hyoscyamine sulfate | 0.15 |
| 2 | Mannitol | 88.90 |
| 3 | Crospovidone | 5.00 |
| 4 | Mint flavor | 0.88 |
| 5 | Colloidal silicon dioxide | 2.07 |
| 6 | Magnesium stearate | 3.00 |
| 7 | Purified water | q.s. |

Procedure:

Hyoscyamine sulfate was dissolved in purified water. Mannitol was granulated with the use of solution of hyoscyamine sulfate. The granules were dried and mixed with crospovidone, mint flavor and colloidal silicon dioxide. The mixture was lubricated with magnesium stearate. The lubricated blend was compressed into tablets.

The tablets of comparative Example 1 were charged on stability in HDPE pack at 40° C. and 75% relative humidity for 3 months. The results of stability study summarized in Table 3B show that the tablets generate impurities when stored in the conditions described above.

TABLE 3B

| Impurity | Initial | 1 Month | 3 Months |
|---|---|---|---|
| DL-tropic acid | ND* | 0.82 | 0.88 |
| 7-hydroxy hyoscyamine | ND | 0.07 | 0.1 |
| 6-hydroxy hyoscyamine | ND | ND | ND |
| Scopolamine | ND | ND | ND |
| Norhyoscyamine | ND | ND | ND |
| Apoatropine | 0.05 | 0.31 | 1.33 |
| Littorine | ND | ND | 0.02 |
| Maximum unknown | ND | 0.15 | 0.15 |
| Total impurities | 0.19 | 0.67 | 1.47 |

*ND = Not Detected

While the invention has been described in terms of its specific embodiments, certain modifications and equivalents will be apparent to those skilled in the art and are intended to be included within the scope of the invention.

We claim:

1. A stable orally disintegrating tablet comprising hyoscyamine or a pharmaceutically acceptable salt thereof and one or more amino acids, wherein the tablet comprises about 10-50% w/w of the amino acid.

2. The stable orally disintegrating tablet according to claim 1, wherein the hyoscyamine or a pharmaceutically acceptable salt thereof is hyoscyamine sulfate.

3. The stable orally disintegrating tablet according to claim 1, wherein the tablet comprises about 0.1-1.0% w/w of the hyoscyamine.

4. The stable orally disintegrating tablet according to claim 1, wherein the amino acid comprises one or more of aspargine, alanine, glutamic acid, glycine, proline, threonine or combinations thereof.

5. The stable orally disintegrating tablet according to claim 1, wherein the amino acid is glycine.

6. The stable orally disintegrating tablet according to claim 1, wherein the tablet has a weight of less than about 70 mg.

7. The stable orally disintegrating tablet according to claim 1 further comprising one or more of pharmaceutically acceptable excipients comprising one or more of diluents, fillers/bulking agents, disintegrants, binders, stabilizing agents, antioxidants, glidants, lubricants, sweeteners/taste masking agents, colorants, and flavors.

8. The stable orally disintegrating tablet according to claim 1, wherein the tablet retains at least about 80% of the potency of hyoscyamine after storing the tablet for three months at 40.degree. C. and 75% relative humidity.

9. A stable orally disintegrating tablet comprising:
0.1-1.0% w/w of hyoscyamine sulfate;
50-65% w/w of microcrystalline cellulose;
25-35% w/w of glycine;
1.0-3.0% w/w of aspartame; and
2.0-10% w/w of crospovidone.

10. The stable orally disintegrating tablet according to claim 1 made by a process comprising:

i. preparing an aqueous solution or a suspension of hyoscyamine or a pharmaceutically acceptable salt thereof;

ii. granulating an excipient with the solution or suspension of hyoscyamine;

iii. drying the granules and mixing the granules with an amino acid and one or more pharmaceutically acceptable excipients;

iv. lubricating the mixture obtained; and v. compressing the lubricated mixture to obtain the tablets.

11. The stable orally disintegrating tablet according to claim 1 made by a process comprising:

i. mixing hyoscyamine or a pharmaceutically acceptable salt thereof with one or more pharmaceutically acceptable excipients;

ii. granulating the mixture;

iii. drying the granules and mixing the granules with an amino acid and one or more pharmaceutically acceptable excipients;

iv. lubricating the mixture obtained; and v. compressing the lubricated mixture to obtain the tablets.

12. The stable orally disintegrating tablet according to claim 1 made by a process comprising:

i. mixing hyoscyamine or a pharmaceutically acceptable salt thereof with an amino acid and one or more pharmaceutically acceptable excipients;

ii. granulating the mixture;

iii. drying the granules and mixing the granules with one or more pharmaceutically acceptable excipients;

iv. lubricating the mixture obtained; and v. compressing the lubricated mixture to obtain the tablets.

* * * * *